US006468984B1

(12) United States Patent
Aboud-Pirak et al.

(10) Patent No.: US 6,468,984 B1
(45) Date of Patent: Oct. 22, 2002

(54) DNA VACCINE FOR PROTECTING AN AVIAN AGAINST INFECTIOUS BURSAL DISEASE VIRUS

(75) Inventors: Esther Aboud-Pirak, Kyriat Tiveon (IL); Michael E. Pirak, Kyriat Tiveon (IL); Esther Shaoul, Nesher (IL); Limor Monadeev, Givat-Ella (IL)

(73) Assignee: Innovo Biotechnologies Ltd., Narareth (IL)

( * ) Notice: Subject to any disclaimer, the term of this patent is extended or adjusted under 35 U.S.C. 154(b) by 0 days.

(21) Appl. No.: 09/450,433

(22) Filed: Nov. 30, 1999

Related U.S. Application Data (60) Provisional application No. 60/138,093, filed on Jun. 8, 1999.

(51) Int. Cl.[7] ............ C12N 15/00; A61K 31/70; A01N 63/00
(52) U.S. Cl. .............. 514/44; 435/320.1; 424/93.2
(58) Field of Search .............. 514/44; 435/320.1; 424/278.1

(56) References Cited

U.S. PATENT DOCUMENTS

| | | |
|---|---|---|
| 5,350,575 A | 9/1994 | Azad et al. |
| 5,518,724 A | 5/1996 | Snyder et al. |
| 5,580,859 A | 12/1996 | Felgner et al. |
| 5,589,466 A | 12/1996 | Felgner et al. |
| 5,595,912 A | 1/1997 | Vakharia et al. |
| 5,605,792 A | 2/1997 | Jackwood et al. |
| 5,605,827 A | 2/1997 | Jackwood et al. |
| 5,610,047 A | 3/1997 | Maruta et al. |
| 5,614,409 A | 3/1997 | Azad et al. |
| 5,632,989 A | 5/1997 | Snyder et al. |
| 5,641,490 A | 6/1997 | Paoletti et al. |
| 5,693,622 A | 12/1997 | Wolff et al. |
| 5,733,554 A * | 3/1998 | Audonnet et al. ........ 424/199.1 |
| 5,788,970 A | 8/1998 | Vakharia et al. |

FOREIGN PATENT DOCUMENTS

| | | |
|---|---|---|
| WO | WO 8810298 | 12/1988 |
| WO | WO 9116925 | 11/1991 |
| WO | WO 98/03659 * | 1/1998 |
| WO | WO 98/09646 | 3/1998 |

OTHER PUBLICATIONS

W. French Anderson, "Human gene therapy" 1998, Nature, vol. 392, pp. 25–30.*
Lanzavecchia, A. "Identifying Strategies for Immune Intervention." 1993, Science, vol. 260, pp. 937–944.*
Iwasaki, A. et al., "Enhanced CTL Responses Mediated by Plasmid DNA Immunogens Encoding Costimulatory Molecules and Cytokines." 1997, Journal of Immunology, vol. 158, pp. 4591–4601.*
Davis, H. L. et al., "Direct gene transfer in skeletal muscle: plasmid DNA–based immunization against the hepatitisB virus surface antigen." 1994, Vaccine, vol. 12, pp. 1503–1509.*
Bayliss et al. "A recombinant fowlpox virus that expresses the VP2 antigen of infectious bursal disease virus induces protection against mortality caused by the virus," Arch. Virol. 1991, vol. 120, pp. 193–205, especially abstract, p. 193.
Pearson and Lipman, *Proc. Natl. Acad. Sci (USA)*, 1988, 85:2444–2448.
Chamczynski and Scchi, *Anal. Biochem.*, 1987, 162:156–159.
Sanger et al., *Proc Natl. Acad. Sci.* 74, 1977, pp 5463–5467.
Laemmli, *Nature*, London, 1970, 227, 680–685.
Towbin et al., *Proc. Natl. Acad. Sci. (USA)*, 76, 1979, p. 4350–4354.
Azad et al., *Virology*, 1987, pp. 145–153.
Macreadie and Azad, *Vaccine Science*, 1990, pp. 549–552.
Pitcovski et al., *Avian Diseases* 40, 1996, 753–761.
Robinson et al., *Vaccine* vol. 1, 1993, pp. 957–960.
Kodihalli et al., *J. Virol.*, vol. 71, 1997, pp. 3391–3396.
Vakharia et al., *Vaccine* 2, 452–456, 1994.
Smith and Waterman, *Adv. App. Math.*, 1981, 2:482–489.
Needleman and Wunsch, *J. Mol. Biol.*, 1970, 48:443–453.

* cited by examiner

*Primary Examiner*—Deborah Crouch
*Assistant Examiner*—Joseph T. Woitach
(74) *Attorney, Agent, or Firm*—Eitan, Pearl, Latter & Cohen-Zedek (57) ABSTRACT

This invention provides a vaccine for protecting an avian species against infectious bursal disease virus which comprises an effective immunizing amount of a vector comprising 1) one or more isolated nucleic acids encoding an infectious bursal disease virus polypeptide; and 2) a suitable carrier and/or adjuvant.

10 Claims, 7 Drawing Sheets

FIG.1

```
ATGACAAACC TGCAAGATCA AACCCAACAG ATTGTTCCGT TCATACGGAG
CCTTCTGATG CCAACAACCG CACCGGCGTC CATTCCGGAC GACACCCTAG
AGAAGCACAC TCTCAGGTCA GAGACTCGA  CCTACAATTT GACTGTGGGG
GACACAGGGT CAGGGCTAAT TGTCTTTTTC CCTGGTTTCC CTGGCTCAAT
TGTGGGTGCT CACTACACAC TGCAGAGCAA TGGGAACTAC AAGTTCGATC
AGATGCTCCT GACTGCCCAG AACCTACCGG CCAGCTACAA CTACTGCAGG
CTAGTGAGTC GGAGTCTCAC AGTGAGGTCA AGCACACTCC CTGGTGGCGT
TTATGCACTA AATGGCACCA TAAACGCCGT GACCTTCCAA GGAAGCCTGA
GTGAACTGAC AGATGTTAGC TACAATGGGT TGATGTCTGC AACAGCCAAC
ATCAA
CGACAAAATC GGGAACGTCC TAGTAGGGGA AGGGGTAACC GTCCTCAGCT
TACCCACATC ATATGATCTT GGGTATGTGA GACTCGGTGA CCCCATTCCC
GCTATAGGGC TCGACCCAAA AATGGTAGCA ACATGTGACA GCAGTGACAG
GCCCAGAGTC TACACCATAA CTGCAGCCGA TGATTACCAA TTCTCATCAC
AGTACCAAGC AGGTGGGGTA ACAATCACAC TGTTCTCAGC TAACATCCAT
GCCATCACAA GCCTCAGCAT CGGGGGAGAA CTCGTGTTCC AAACAAGCGT
CCAAGGCCTT ATACTGGGTG CTACCATCTA CCTTATAGGC TTTGATGGGA
CTGCGGTAAT CA
CCAGAGCTGT GGCCGCAGAC AATGGGCTAA CGGCCGGCAC TGACAACCTT
ATGCCATTCA ATATTGTGAT TCCAACCAGC GAGATAACCC AGCCAATCAC
ATCCATCAAA CTGGAGATAG TGACCTCCAA AAGTGGTGGT CAGGCGGGGG
ATCAGATGTC ATGGTCAGCA AGTGGGAGCC TAGCAGTGAC GATCCACGGT
GGCAACTATC CAGGGGCCCT CCGTCCCGTC ACACTCGTAG CCTACGAAAG
AGTGGCAACA GGATCTGTCG TTACGGTCGC CGGGGTGAGC AACTTCGAGC
TGATCCCAAA TCCTGAACTA GCAAAGAACC TGGTCACAGA ATACGGCCGA
TTTGACCCAG GAGCCATGAA CTACACAAAA TTGATACTGA GTGAGAGGGA
CCGTCTTGGC ATCAAGACCG TATGGCCAAC AAGGGAGTAC ACTGACTTTC
GCGAGTACTT CATGGAGGTG GCCGACCTCA ACTCTCCCCT GAAGATTGCA
GGAGCATTTG GCTTCAAAGA CATAATCCGG GCCATAAGGA GGTAATGA
```

FIG.2

```
 5  ATGACAAACC TGCAAGATCA AACCCAACAG ATTGTTCCGT TCATACGGAG
    CCTTCTGATG CCAACAACCG CACCGGCGTC CATTCCGGAC GACACCCTAG
10  AGAAGCACAC TCTCAGGTCA GAGACTCGA  CCTACAATTT GACTGTGGGG
    GACACAGGGT CAGGGCTAAT TGTCTTTTTC CCTGGTTTCC CTGGCTCAAT
    TGTGGGTGCT CACTACACAC TGCAGAGCAA TGGGAACTAC AAGTTCGATC
15
    AGATGCTCCT GACTGCCCAG AACCTACCGG CCAGCTACAA CTACTGCAGG
    CTAGTGAGTC GGAGTCTCAC AGTGAGGTCA AGCACACTCC CTGGTGGCGT
20  TTATGCACTA AATGGCACCA TAAACGCCGT GACCTTCCAA GGAAGCCTGA
    GTGAACTGAC AGATTAATGA
```

FIG.3

```
    ATGGTTAGTACAGATCAGACAAACGATCGCAGCGATGACGAACCTGCAAGATCA
 5
    AACCCAACAG ATTGTTCCGT TCATACGGAG CCTTCTGATG CCAACAACCG

ACCGGCGTC CATTCCGGAC GACACCCTAG  AGAAGCACAC TCTCAGGTCA
    GAGACCTCGA CCTACAATTT GACTGTGGGG GACACAGGGT CAGGGCTAAT
10  TGTCTTTTTC CCTGGTTTCC CTGGCTCAAT TGTGGGTGCT CACTACACAC
    TGCAGAGCAA TGGGAACTAC AAGTTCGATC AGATGCTCCT GACTGCCCAG
    AACCTACCGG CCAGCTACAA CTACTGCAGG CTAGTGAGTC GGAGTCTCAC
    AGTGAGGTCA AGCACACTCC CTGGTGGCGT TTATGCACTA AATGGCACCA
    TAAACGCCGT GACCTTCCAA GGAAGCCTGA GTGATAA
15
```

FIG.4

5   ATGG AGGTGGCCGA CCTCAACTCT CCCCTGAAGA TTGCAGGAGC ATTTGG
    CTTCAAAGACATAA TCCGGGCCCT AAGGAGGATC GCTGTGCCGG TGGTCT
10  CTACATTGTTCCCA CCCGCCGCTC CCTAGCCCA TGCAATTGGG GAAGGTG
    GCCGCGTCAGGAA AAGCAAGAGC TGCCTCAGGC CGCATAAGGC AGCTAAC
    TCTCGCCGCCGAC AAGGGGTACG AGGTAGTCGC GAATCTGTTT CAGGTGCC
15  CCAGAATCCTGT AGTCGACGGG ATTCTCGCCT CACCTGGGAT ACTCCGCGG
    CGCACACAACC TCGACTGCGT GTTGAGAGAG GGTGCCACGC TATTCCCTGT
20  GGTCATCACG ACAGTGGAAG ATGCCATGAC ACCCAAAGCA CTGAACAGCA
    AAATGTTTGC TGTCATTGAA GGCGTGCGAG AAGATCTCCA ACCTCCATCT
    CAAAGAGGAT CCCTTCATACG AACTCTCTAA TGA
25

DNA VACCINE FOR PROTECTING AN AVIAN AGAINST INFECTIOUS BURSAL DISEASE VIRUS

This application claims benefit to provisional application 60/138,093 filed Jun. 8, 1999.

FIELD OF INVENTION

This invention provides a vaccine for protecting an avian against an avian pathogen such as Infectious Bursal Disease Virus, Newcastle Disease Virus, or Mycoplasma gallisepticum, which comprises an effective immunizing amount of a vector comprising an isolated nucleic acid encoding Infectious Bursal Disease Virus peptides such as VP1, VP1s1, VP1s2, VP2, VP2S, VP3, VP4, VP4S and VP5, and a suitable carrier. Further, this invention provides a method for enhancing an avian immune response which comprises administering to the avian an effective amount of the vaccine and a method of immunizing an avian comprising administrating to the avian an effective amount of the vaccine.

BACKGROUND OF THE INVENTION

Infectious bursal disease (IBD) has been observed in chickens since 1957. Birds which survive the disease are permanently immunosuppressed. Therefore they are more susceptible to other disease causing agents and do not respond adequately to vaccinations which are an essential part of poultry management systems. The bursa of Fabricius (BF) is the primary target organ of IBDV. The virus replicates in immature bursa-derived lymphocytes (B-lymphocytes) of chickens. Chickens infected with IBDV at one day of age are completely devoid of serum immunoglobulin G (IgG) and produce only monomeric IgM. A permanent decrease in the number of peripheral blood B cells was observed following an IBDV infection.

Infectious bursal disease virus (IBDV) causes immunosuppression of the humoral immune system of young chickens. Antibodies produced as a result of an IBDV infection will protect birds from the disease. Thus, control of this disease is achieved by vaccination with live-attenuated viruses. Diagnosis of IBDV is accomplished using assays such as immunofluorescence and antigen capture ELISA, which can detect presence, but not identify serotype, antigenic subtype or virulence of the virus. In some strains of the virus they constitute 50 and 50% of the virus protein respectively. Neutralizing epitopes were detected on VP2 and VP3. Antibodies to these epitopes were found to passively protect chickens (Azad et al. Virology m pp 145–153 1987). Several attempts were made to produce recombinant vaccines. VP2 expressed in *E. coli* failed to promote neutralizing antibodies in chickens. However when expressed in yeasts VP2 conferred protection (Macreadie and Azad Vaccine S pp 549–552 1990). The production of large amounts of recombinant VP2 in a baculovirus expression system was shown to protect chicken against disease (Pitcovski et al. Avian Diseases 40: 753–761 1996).

An effective IBD prevention and control program must involve an effective breeder vaccination program, an effective biosecurity program, and an effective broiler vaccination program. Immunization of breeders is an important part of the IBD control program. Antibodies produced by the hen are passed through the egg to the broiler chick. These maternal antibodies, if present in adequate levels, protect the chicks against subclinical IBD. An example of a comprehensive breeder vaccination program where subclinical IBD is a problem might have a vaccine schedule such as this: at 12 to 15 days of age IBD live; at 30 to 33 days of age IBD live; at 85 days of age IBD live or inactivated; and at 120 days of age IBD inactivated. Revaccinate at 38 to 42 weeks of age with an inactivated IBD vaccine if breeder titers are low or of poor uniformity. Routinely monitor breeder IBD antibody titers to ensure vaccines are administered properly and that the chickens respond appropriately.

Three categories of vaccines, based on their pathogenicity, have been described: 1) mild, 2) intermediate, and 3) virulent. The intermediate type IBD vaccines are most commonly used. These vaccines can stimulate the broiler to produce antibodies earlier than the mild-type vaccines, without significant damage to the BF as may occur with the virulent type vaccines. The timing of broiler vaccination depends on the level of maternal antibody present in the chicks. High levels of maternal antibody at the time of vaccination will neutralize the vaccine virus. Thus, only a limited active immune response results, and chickens will be susceptible to disease as maternal titers decrease. If low levels of maternal IBD titers are present in the chicks, vaccination may not be effective on farms contaminated with virulent field virus. Approximately 10 to 12 days are required after vaccination for chickens to develop minimal protective titers. During this "lag time," chickens are susceptible to IBD. Hence, the advantage of a vaccine that can be given in the presence of maternal antibodies.

In addition, virulent IBD viruses are able to break through higher maternal titers than milder vaccine viruses. Thus, if IBD field virus contamination on a broiler farm is high, nor broiler vaccination can stimulate protection in the flock before damage occurs. If the maternal antibody titer is not uniform in the broiler flock, multiple costly vaccinations will be required. For example, some producers may vaccinate broilers at one day of age and again at fourteen days of age. This multiple IBD vaccination would be recommended when maternal titers are poorly uniform, which results from poor vaccine administration in breeders or when mixing broilers from different breeder flocks. In a recent study, even a group of breeders that had fairly uniform IBD titers had chicks with titers that were variable, with many chicks have little or no maternal antibody protection. Although the 1 day of age vaccination would be of little direct benefit to broilers with high maternal titer levels, multiple vaccinations would provide some protection to chicks with lower levels of maternal antibody and would help reduce replication of IBD field virus and subsequent shed in the poultry house environment.

IBDV is highly contagious and can spread quickly through a flock. Infection is distributed through contaminated feed and water. The disease is commonly diagnosed in birds between 3 and 6 weeks old. Gross lesions can be seen for the most part on the bursa of Fabricius. The bursa may be swollen, or show signs of hemorrhage. In some cases, however, no lesions are observed and the bursa shrinks in size. Chickens with the disease exhibit anorexia, depression, watery diarrhea, ruffled feathers, soiled vent feathers, vent picking, and death. The course is usually 5–7 days. Protection of chickens from IBD through the use of vaccines is complicated by the presence of two serotypes and several antigenic subtypes of the virus. Vaccination with a given antigenic subtype of IBDV serotype I will not always protect chicks from the disease when the challenge virus is a different antigenic subtype.

It is possible to alter cells in a selected way by putting foreign DNA into them. It was shown already at the mid 1950S that cells could take up nucleic acids extracted from viruses and express them as proteins. Since then efforts were directed to improve the efficacy of the delivery—transfection—of functional genes to cells. The main obstacle to DNA uptake was thought to be the negative electrical charge of the nucleic acid. The DNA molecule is repelled from the membranes of the cells because they are negatively charged. Techniques were developed to neutralize the DNA, negative charge, among them is the treatment with calcium phosphate or DEAE dextran.

Advances in the field of DNA transfection took place with the development of recombinant DNA technique. It allowed the insertion of individual genes from cells into plasmids. The delivery of the recombinant plasmids derived from the bacteria into cultured eucaryotic cells allowed the expression of the inserted genes and the production of recombinant proteins in the cell at will. Industry has made use of the technique to produce a growing list of recombinant proteins of medicinal value like insulin, factor VIII, growth factors and cytokines. Advances in the field of DNA transfection—including the development of gene carrying liposomes—lipid micelles "loaded" with recombinant plasmids brought about hopes that the technique may be applied for gene therapy—the introduction into the body of genes that produce proteins of therapeutic value. It is not clear yet whether this approach can bring about the in vivo expression of therapeutic amounts of the recombinant protein, but at the neater term it seems to have promise for use in vaccines. Even minute amounts of protein can stimulate a protective immune response against infectious agents parasites.

In the last three years, DNA vaccines have burst onto the scene as radically new like viruses, bacteria and approach to infectious disease prophylaxis. One of the most surprising and important features of DNA immunization is that purified "naked" DNA appears to be taken up and expressed by cells in vivo with much greater efficiency than would have been. Not much has been reported in the field of chicken infectious diseases. A report on the protection of chicken against a lethal influenza virus challenge with plasmid DNA by Robinson et al. (Vaccine vol. 1 pp 957–960 1993) opened the avenue for the improvement of protective efficacy in chicken. Chicken injected intramuscularly twice with plasmid DNA expressing heamagglutinin (HA) were protected from lethal challenge with a virulent influenza virus. A more recent work from the same group (Kodihalli et al. J. Virol. Vol 71 pp 3391–3396 1997) shows that the HA DNA vaccine conferred 95% cross-protection against challenge with lethal antigenic variants that differ from the primary antigen by 11 to 13%. Several attempts were made to produce recombinant vaccines. VP2 expressed in E. coli failed to promote neutralizing antibodies in chickens. However when expressed in yeasts VP2 conferred protection (Macreadie and Azad Vaccine S pp 519–552 1990). Production of recombinant VP2 using the baculovirus expression system (Piteovski et al. Avian Diseases 40: 753–761 1996 and Goodwin M A et al. Vaccine 1994 12 452–456 1994.) has been reported.

SUMMARY OF THE INVENTION

This invention provides a vector comprising one or more isolated nucleic acids encoding an infectious bursal disease virus polypeptide, or a mutant or variant thereof, wherein said nucleic acid is under the control of a promoter. This invention provides a vector comprising one or more isolated nucleic acids encoding an infectious bursal disease VP1, VP1s1, VP1s2, VP2, VP2S, VP3, VP4, VP4S and VP5 or a mutant or variant thereof, wherein said nucleic acid is under the control of a promoter.

This invention provides a vaccine for protecting an avian against an avian pathogen such as Infectious Bursal Disease Virus, Newcastle Disease Virus, or Mycoplasma gallisepticum, which comprises an effective immunizing amount of a vector comprising 1) one or more isolated nucleic acids encoding an infectious bursal disease virus polypeptide, or a mutant or variant thereof, wherein said nucleic acid is under the control of a promoter; and 2) a suitable carrier and/or adjuvant.

This invention provides a vaccine for protecting an avian against an avian pathogen such as Infectious Bursal Disease Virus, Newcastle Disease Virus, or Mycoplasma gallisepticum, which comprises an effective immunizing amount of a vector comprising 1) one or more isolated nucleic acids encoding an infectious bursal disease VP1, VP1s1, VP1s2, VP2, VP2S, VP3, VP4, VP4S and VP5, or a mutant or variant thereof, wherein said nucleic acid is under the control of a promoter; and 2) a suitable carrier and/or adjuvant. Further, it is contemplated that the vaccine comprises a mixture of VP2 and VP2s.

This invention provides a method for enhancing an avian immune response which comprises administering to the avian an effective amount of the vaccine and a method of immunizing an avian comprising administering to the avian an effective amount of the vaccine.

BRIEF DESCRIPTION OF THE FIGURES

FIG. 1: Schematic of plasmid P-INN-001 comprising nucleic acid encoding IBDV VP2, IBDV VP2S, and/or IBDV VP5. P-INN-001 contains a human CMV immediate early promoter, T7 promoter/priming site, multiple cloning site, BGH reverse priming site, BGH poly A, f1 origin of replication and colE1 origin. Multiple cloning site and Antibiotic resistance gene for selection of vector in E. coli.

FIG. 2: The isolated nucleic acid encoding Infectious Bursal Disease Virus VP2 is set forth in SEQ ID NO.1.

DETAIL DESCRIPTION OF THE INVENTION

This invention provides a novel DNA plasmid vaccination method designed to protect poultry from infectious diseases is demonstrated herein. The method is related to DNA-mediated vaccination and it involves the direct introduction of a vector DNA encoding an antigenic protein which is then expressed within cells of the organism. This leads to surprisingly strong immune response, involving both the humoral and cellular arms of the immune system.

This invention provides a vector comprising one or more isolated nucleic acids encoding an infectious bursal disease virus polypeptide, wherein said nucleic acid is under the control of a promoter. In one embodiment the isolated nucleic acid encodes infectious bursal disease virus VP1. In one embodiment the isolated nucleic acid encodes infectious bursal disease virus VP1s1. In one embodiment the isolated nucleic acid encodes infectious bursal disease virus VP1s2. In one embodiment the isolated nucleic acid encodes infectious bursal disease virus VP2. In another embodiment the isolated nucleic acid encodes infectious bursal disease virus VP2S. In another embodiment the isolated nucleic acid encodes infectious bursal disease virus VP3. In another embodiment the isolated nucleic acid encodes infectious bursal disease virus VP4. In another embodiment the isolated nucleic acid encodes infectious bursal disease virus VP5. In another embodiment the vector comprises two or more of the infectious bursal disease virus VP1–5.

This invention provides a vaccine for protecting an avian against an Infectious Bursal Disease virus which comprises an effective immunizing amount of a vector comprising 1) one or more isolated nucleic acids encoding an infectious bursal disease virus polypeptide, wherein said nucleic acid is under the control of a promoter; and 2) a suitable carrier and/or adjuvant. In one embodiment the isolated nucleic acid encodes infectious bursal disease virus VP1. In one embodiment the isolated nucleic acid encodes infectious bursal disease virus VP1s1. In one embodiment the isolated nucleic acid encodes infectious bursal disease virus VP1s2. In one embodiment the isolated nucleic acid encodes infectious bursal disease virus VP2. In another embodiment the isolated nucleic acid encodes infectious bursal disease virus VP2S. In another embodiment the isolated nucleic acid encodes infectious bursal disease virus VP3. In another embodiment the isolated nucleic acid encodes infectious bursal disease virus VP1. In another embodiment the isolated nucleic acid encodes infectious bursal disease virus VP5. In another embodiment the vaccine comprises two or more of the infectious bursal disease virus VP1–5. Further the vaccine may comprise one or more of the vectors which have been linearized by appropriate digestion at particular restriction nuclease sites.

Figure 1:
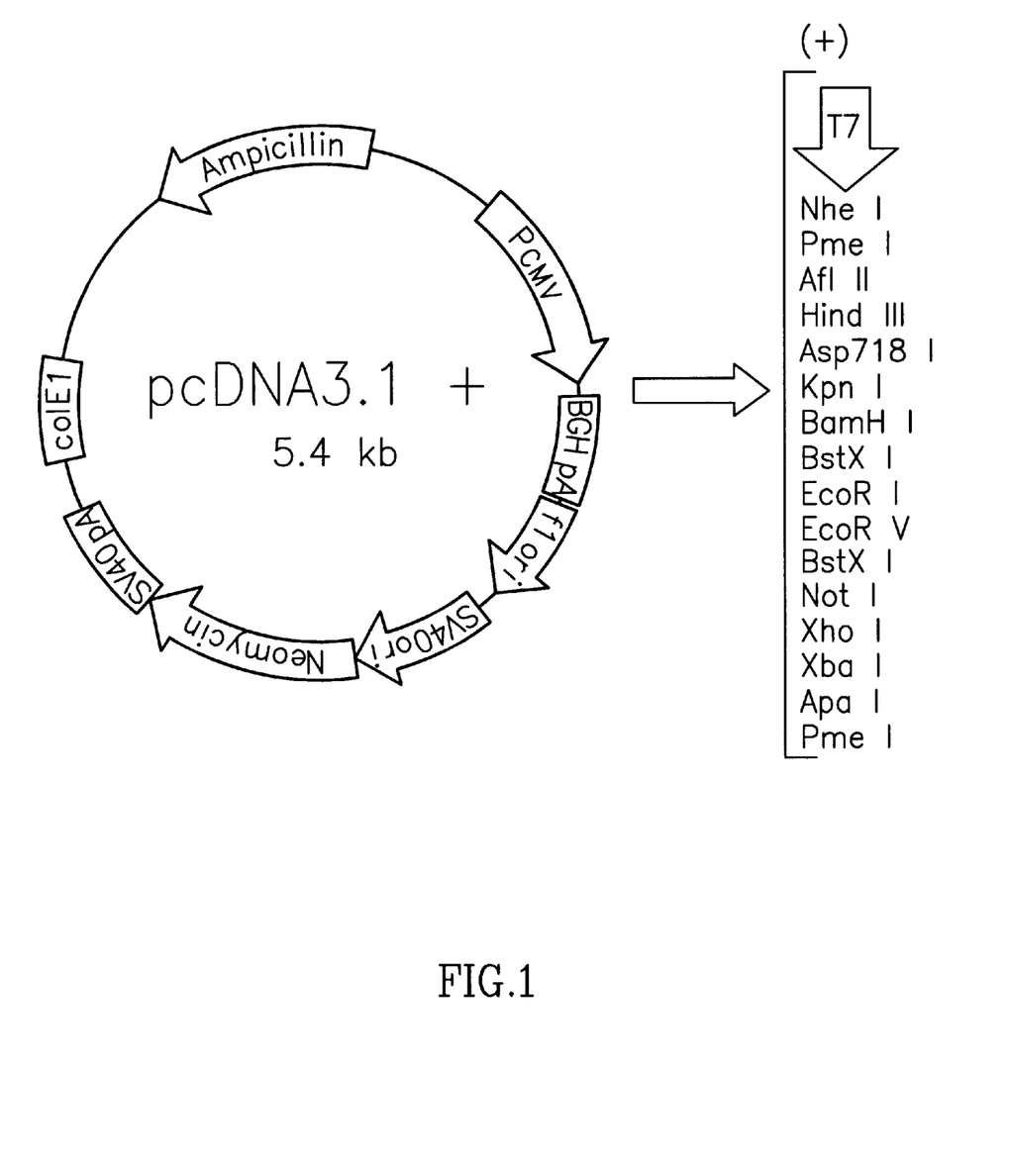
Figure 3:
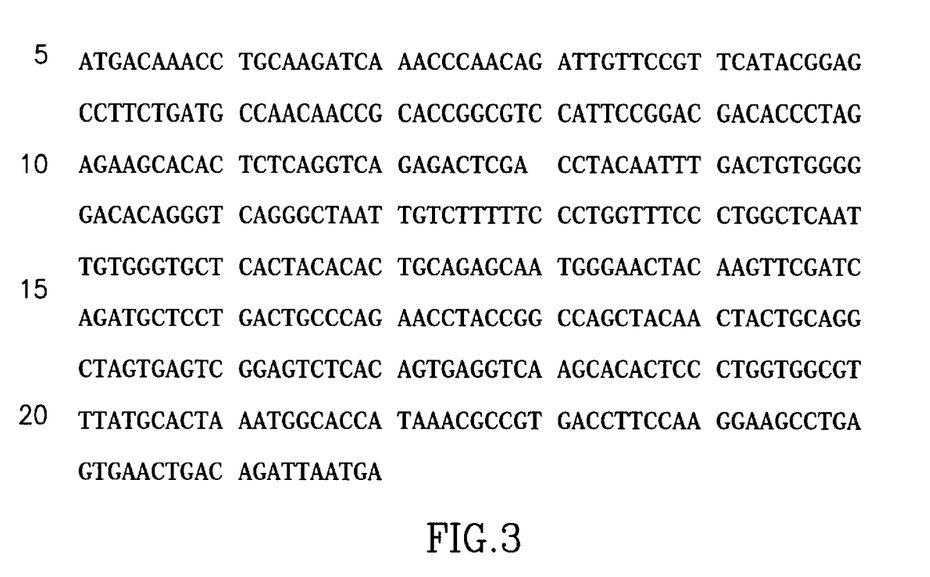
FIG. 3: The isolated nucleic acid encoding Infectious Bursal Disease Virus VP2S is set forth in SEQ ID NO.2.
Figure 4:
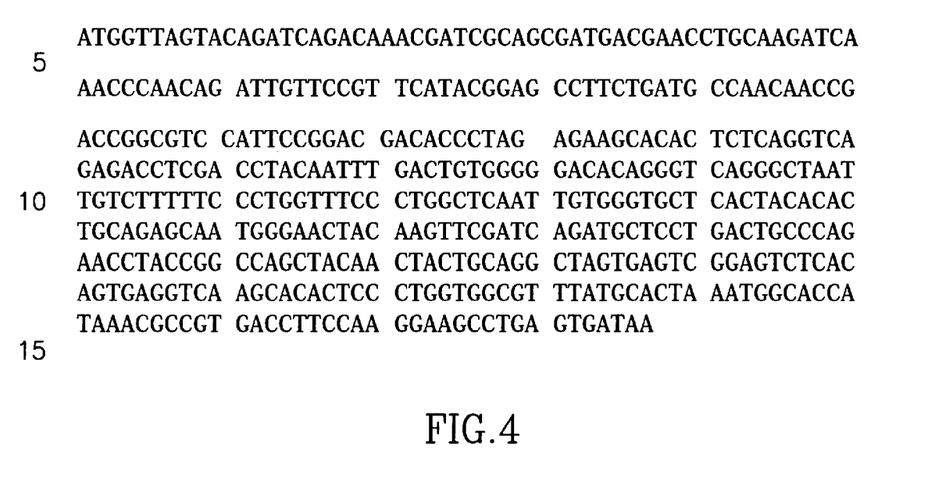
FIG 4: The isolated nucleic acid encoding Infectious Bursal Disease Virus VP5 is set forth in SEQ ID NO.3 as shown in FIG. 4.
Figure 5:
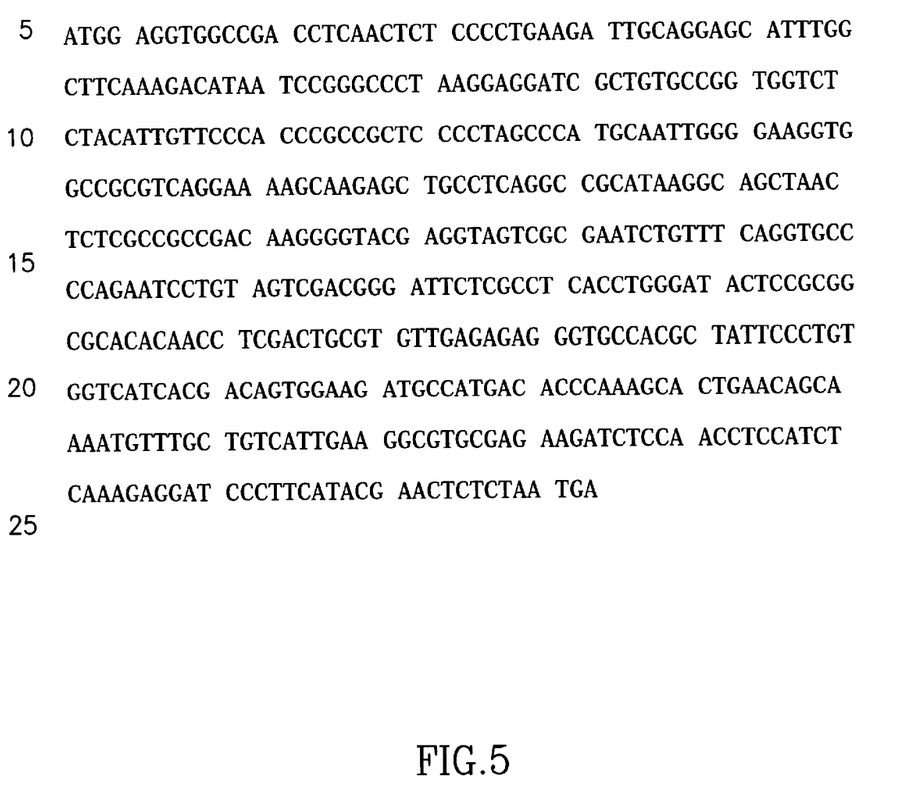
FIG. 5: The isolated nucleic acid encoding Infectious Bursal Disease Virus VP4s is set forth in SEQ ID NO.4 as shown in FIG. 5.
Figure 6:
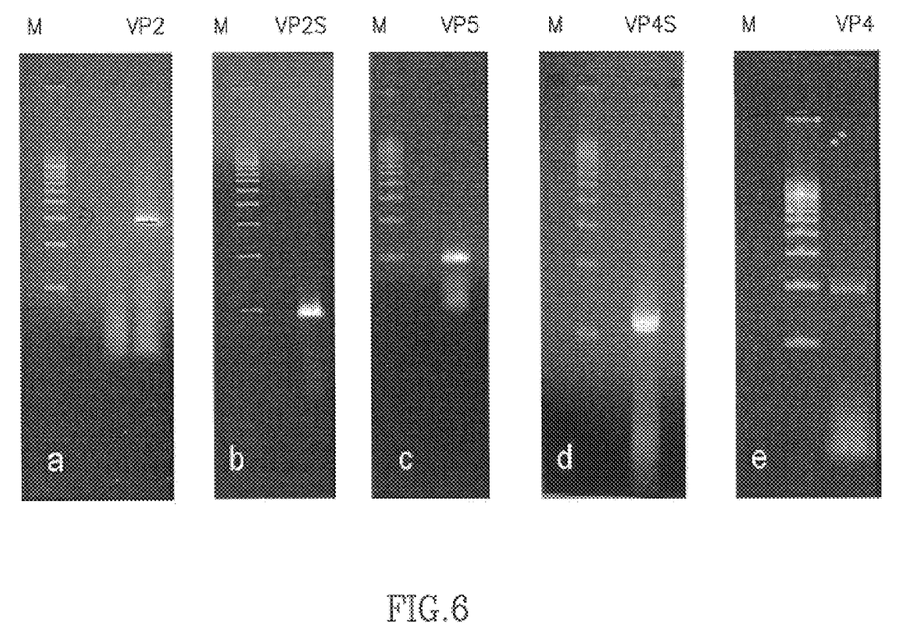
FIG. 6: PCR results for synthesis of first strand specific cDNAs and it's amplification. The procedure was carried out as described in materials and methods. 500 bp ladder (Bio-Rad) was used as M. W marker. PCR products were separated on 0.8% agarose gel a: VP2, b: VP2S, c: VP5, d: VP4S, and e: VP4
Figure 7:
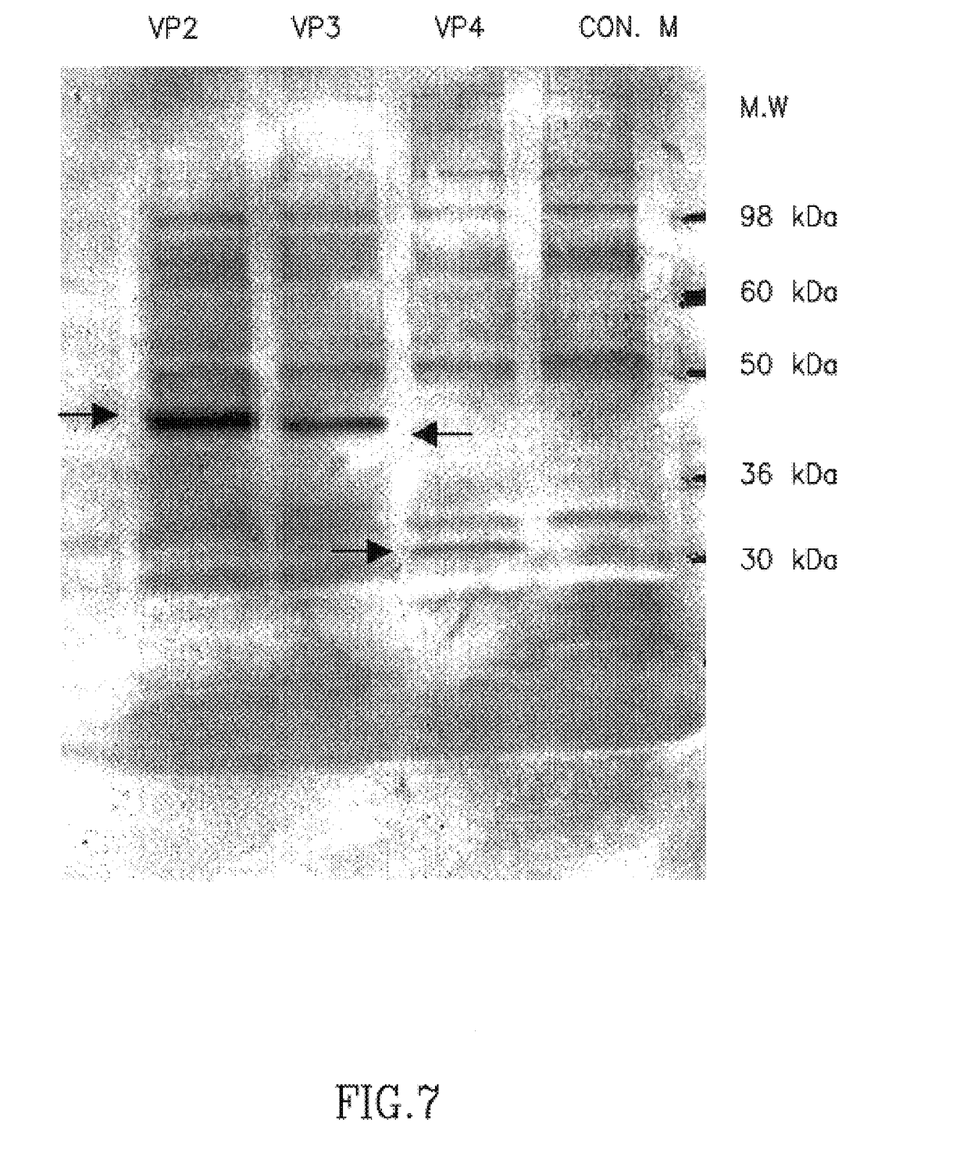
FIG. 7: In Vitro translation was preformed as described in materials and methods Samples were separated on 15% SDS-PAGE, (Bio-Rad) prestained, broad range marker were used as M. W standards (M). Lane 1 pcDNA 3.1 plasmid (control). Lane 2 VP2 cDNA cloned in pcDNA3.1.
Figure 8A:
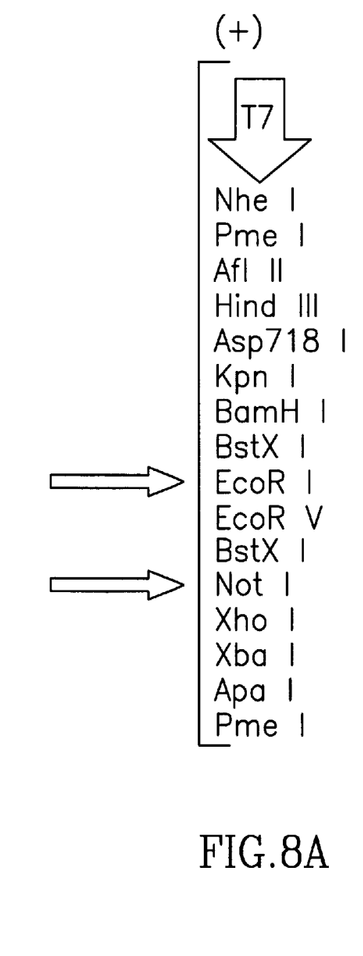
FIGS. 8A–8C: Restriction endonuclease sites for ligation of DNA fragments to a vector
Figure 8B:
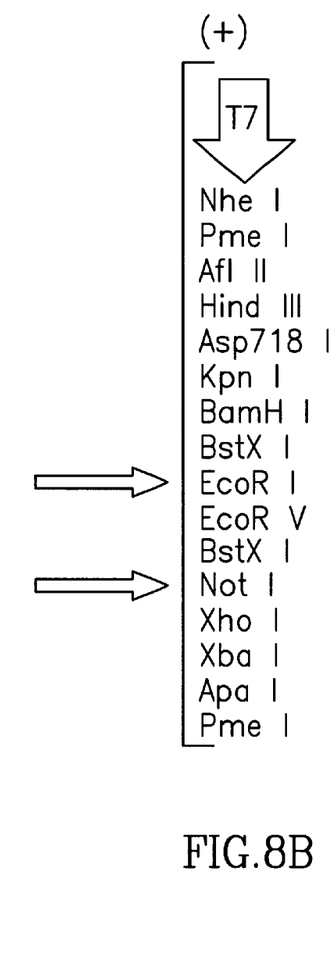
Figure 8C:
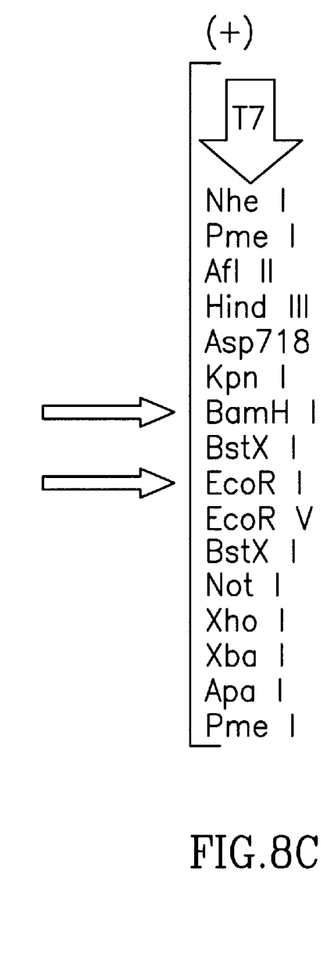

The isolated nucleic acid encoding infectious bursal disease virus VP2 is set forth in SEQ ID NO.1 as shown in FIG. 2. The isolated nucleic acid encoding infectious bursal disease virus VP2S is set forth in SEQ ID NO.2 as shown in FIG. 3. The isolated nucleic acid encoding infectious bursal disease virus VP5 is set forth in SEQ ID NO.3 as shown in FIG. 4. The isolated nucleic acid encoding infectious bursal disease virus VP4s is set forth in SEQ ID NO.4 as shown in FIG. 5.

As contemplated herein analogs, fragments, mutants, substitutions, synthetics, variants of the isolated nucleic acid encoding VP1, VP2, VP2X, VP2S, VP3, VP4, VP5 and/or miemtics or polyprotein. Such are known to those skilled in the art. For example, U.S. Pat. Nos. 5,614,409, 5,788,970; 5,605,792; 5,518,724; 5,595,912; 5,641,490; 5,350,575; 5,610,047; 5,605,827 and WO9116925, and WE8810298, which are incorporated in their entirety herein.

Mutations can be made in a nucleic acid encoding the polypeptide such that a particular codon is changed to a codon which codes for a different amino acid. Such a mutation is generally made by making the fewest nucleotide changes possible. A substitution mutation of this sort can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e. by changing the codon from an amino acid belonging to a grouping of amino acids having a particular size or characteristic to an amino acid belonging to the same grouping). Such a conservative change generally leads to less change in the structure and function of the resulting protein. A non-conservative change is more likely to alter the structure, activity or function of the resulting protein. The present invention should be considered to include sequences containing conservative changes which do not significantly alter the activity or binding characteristics of the resulting protein. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charges (basic) amino acids include arginine, lysine and histidine. The negatively charged (acidic) amino acids include aspartic acid and glutamic acid. Such alterations will not be expected to affect apparent molecular weight as determined by polyacrylamide gel electrophoresis, or isolelectric point. Further, other positions may be varied by themselves as long as the antigenic binding ability of the polypeptide is not destroyed.

In a preferred embodiment the vaccine comprises a vector comprising an isolated nucleic acid encoding an infectious bursal disease VP2, wherein said nucleic acid is under the control of a promoter is designated P-INN-001. P-INN-001 was deposited on Dec. 29, 1999 under ATCC Accession No. PTA-1101 pursuant to the Budapest Treaty on the International Deposit of Microorganisms for the Purposes of Patent Procedure with the Patent Culture Depository of the American Type Culture Collection.

A "nucleic acid" refers to the phosphate ester polymeric form of ribonuclcosides (adenosine, guanosine, pridine or cytidine; "RNA molecules") or deoxyrubonucleosides (deoxyadenosine, deoxyadenosine, deoxythymidine, or deoxycytidine; "DNA molecules") in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structures of the molecule, and does not limit it to any particular tertiary forms. Thus, this term includes double-stranded DNA found, inter alia, in linear or circular DNA molecules (e.g., restriction fragments), plasmids and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

The following terms are used to describe the sequence relationships between two or more nucleic acid molecular or polynucleotides: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing or may comprise a complete cDNA or gene sequence. Optimal alignment of sequences for aligning a comparison window may be conducted by the local homology algorithm of Smith and Waterman (1981) *Adv. Appl. Math.* 2:482, by the homology alignment algorithm of Needleman and Wunsch (1970) *J. Mol. Biol.* 48:443, by the search for similarity method of Pearson and Lipman (1988) *Proc. Natl. Acad. Sci.* (USA) 85:2444, or by computerized implementations of these algorithms (GAP, BESTFIT, FASTA, and TFASTA in the Wisconsin Genetics Software Package Release 7.0, Genetics Computer Group, 575 Science Dr., Madison Wis.).

"Substantial identity" or "substantial sequence identity" mean that two peptide sequences, when optimally aligned, such as by the programs GAP or BESTFIT using default gap which share at least 90 percent sequence identity, preferably a least 95 percent sequence identity, more preferably at least 99 percent sequence identity or more. "Percentage amino acid identity" or "percentage amino acid sequence identity" refers to a comparison of the amino acids of two polypeptides which, when optimally aligned, have approximately the designated percentage of the same amino acids. For example, "95% amino acid identity" refers to a comparison of the amino acids of two polypeptides which when optimally aligned have 95% amino acid identity. Preferably, residue positions which are not identical differ by conservative amino acid substitutions. For example, the substitution of amino acids having similar chemical properties such as charge or polarity are not likely to effect the properties of a protein. Examples include glutamine for asparagine or glutamic acid for aspartic acid.

In another embodiment of the nucleic acid has a nucleotide sequence having at least 75% similarity with the nucleic acid coding sequence of SEQ ID NO:1. In another embodiment the nucleic acid has a nucleotide sequence having at least 85% similarity with the nucleic acid coding sequence of SEQ ID NO:1. In another embodiment the nucleic acid has a nucleotide sequence having at least 90% similarity with the nucleic acid coding sequence of SEQ ID NO:1. In another embodiment the nucleic acid has a nucleotide sequence having at least 90% similarity with the nucleic acid coding sequence of SEQ ID NO:1. In another embodiment the nucleic acid has a nucleotide sequence having at least 95% similarity with the nucleic acid coding sequence of SEQ ID NO:1.

In another embodiment the nucleic acid has a nucleotide sequence having at least 75% similarity with the nucleic acid coding sequence of SEQ ID NO:2. In another embodiment the nucleic acid has a nucleotide sequence having at least 85% similarity with the nucleic acid coding sequence of SEQ ID NO:2. In another embodiment the nucleic acid has a nucleotide sequence having at least 90% similarity with the nucleic acid coding sequence of SEQ ID NO:2. In another embodiment the nucleic acid has a nucleotide sequence having at least 90% similarity with the nucleic acid coding sequence of SEQ ID NO:2. In another embodiment the nucleic acid has a nucleotide sequence having at least 95% similarity with the nucleic acid coding sequence of SEQ ID NO:2.

In another embodiment the nucleic acid has a nucleotide sequence having at least 75% similarity with the nucleic acid coding sequence of SEQ ID NO:3. In another embodiment the nucleic acid has a nucleotide sequence having at least 85% similarity with the nucleic acid coding sequence of SEQ ID NO:3. In another embodiment the nucleic acid has a nucleotide sequence having at least 90% similarity with the nucleic acid coding sequence of SEQ ID NO:3. In another embodiment the nucleic acid has a nucleotide sequence having at least 90% similarity with the nucleic acid coding sequence of SEQ ID NO:3. In another embodiment the nucleic acid has a nucleotide sequence having at least 95% similarity with the nucleic acid coding sequence of SEQ ID NO:3.

In another embodiment the nucleic acid has a nucleotide sequence having at least 75% similarity with the nucleic acid coding sequence of SEQ ID NO:4. In another embodiment the nucleic acid has a nucleotide sequence having at least 85% similarity with the nucleic acid coding sequence of SEQ ID NO:4. In another embodiment the nucleic acid has a nucleotide sequence having at least 90% similarity with the nucleic acid coding sequence of SEQ ID NO:4. In another embodiment the nucleic acid has a nucleotide sequence having at least 90% similarity with the nucleic acid coding sequence of SEQ ID NO:4. In another embodiment the nucleic acid has a nucleotide sequence having at least 95% similarity with the nucleic acid coding sequence of SEQ ID NO:4.

In another embodiment the nucleic acid has a nucleotide sequence having at least 75% similarity with the nucleic acid coding sequence of SEQ ID NO:5. In another embodiment the nucleic acid has a nucleotide sequence having at least 85% similarity with the nucleic acid coding sequence of SEQ ID NO:5. In another embodiment the nucleic acid has a nucleotide sequence having at least 90% similarity with the nucleic acid coding sequence of SEQ ID NO:5. In another embodiment the nucleic acid has a nucleotide sequence having at least 90% similarity with the nucleic acid coding sequence of SEQ ID NO:5. In another embodiment the nucleic acid has a nucleotide sequence having at least 95% similarity with the nucleic acid coding sequence of SEQ ID NO:5.

As defined herein an "isolated" or "substantially pure" nucleic acid (e.g., an RNA, DNA or a mixed polymer) is one which is substantially separated from other cellular components which naturally accompany a native human sequence or protein, e.g., ribosomes, polymerases, many other human genome sequences and proteins. The term embraces a nucleic acid sequence or protein which has been removed from its naturally occurring environment, and includes recombinant or cloned DNA isolates and chemically synthesized analogs or analogs biologically synthesized by heterologous systems.

The term "vector", refers to viral expression systems, autonomous self-replicating circular DNA, plasmid, and includes both expression and nonexpression plasmids. Where a recombinant microorganism or cell culture is described as hosting an "expression vector," this includes both extrachromosomal circular DNA and DNA that has been incorporated into the host chromosome(s). Where a vector is being maintained by a host cell, the vector may either be stably replicated by the cells during mitosis as an autonomous structure, or is incorporated within the host's genome. Such vectors which may be used are pcDNA3.1(+) and pcDNA3.1(−) (commercially available from Invitrogen).

The term "plasmid" refers to an autonomous circular DNA molecule capable of replication in a cell, and includes both the expression and nonexpression types. Where a recombinant microorganism or cell culture is described as hosting an "expression plasmid", this includes latent viral DNA integrated into the host chromosome(s). Where a plasmid is being maintained by a host cell, the plasmid is either being stably replicated by the cells during mitosis as an autonomous structure or is incorporated within the host's genome. The plasmid or vector as contemplated herein comprises a leader sequence which are known to those skilled in the art.

This vector or plasmid may also further comprise a second isolated nucleic acid which encodes a screenable marker and/or a polypeptide. For purposes of this invention, a "polypeptide which is a detectable marker" includes but is not limited to: the bimer, trimer and tetramer form of the polypeptide. *E. coli* beta-galactosidase is a tetramer composed of four polypeptides or monomer sub-units.

Further, the nucleic acid which encodes a polypeptide is selected from a group consisting of a: cytokine, Infectious bovine rhinotracheitis virus gE, bovine respiratory syncytial virus attachment protein (BRSV G), bovine respiratory syncytial virus fusion protein (BRSV F), bovine respiratory syncytial virus nucleocapsid protein (BRSV N), bovine parainfluenza virus type 3 fusion protein, and the bovine parainfluenza virus type 3 hemagglutinin neuraminidase, marek's disease virus glycoprotein B, marek's disease virus glycoprotein D, newcastle disease virus hemagglutinin, newcastle disease virus neuraminidase, newcastle disease virus fusion, infectious bursal disease virus VP1, infectious bursal disease virus VP2, infectious bursal disease virus VP3, infectious bursal disease virus VP4, infectious bursal disease virus VP5, infectious bursal disease virus polyprotein, infectious bronchitis virus spike, and infectious bronchitis virus matrix and chick anemia virus.

Such may also be derived or derivable from avian encephalomyelitis virus, avian reovirus, avian paramyxovirus, avian influenza virus, avian adenovirus, fowl pox virus, avian coronavirus, avian rotavirus, chick anemia agent, Salmonella spp., *E. coli.*, Pasteurella spp., Bordetella spp. Eimeria spp. Histomonas spp., Trichomonas spp., poultry nematodes, cestodes, trematodes, poultry mites/lice, poultry protozoa.

As contemplated herein cytokines, include but are not limited to the following: chicken myclomonocytic growth factor (cMGF) or chicken interferon (cIFN), transforming growth factor beta, epidermal growth factor family, fibroblast growth factors, hepatocyte growth factor, insulin-like growth factor, vascular endothelial growth factor, interleukin 1, IL-1 receptor antagonists, interleukin-2, interleukin-3, interleukin-4, interleukin-5, interleukin-6, IL-6 soluble receptor, interleukin-7, interleukin-8, interleukin-9, interleukin-10, interleukin-11, interleukin-12, interleukin-13, angiogenin, chemokines, colony stimulating factors, granulocyte-macrophage colony stimulating factors, erythropoietin, interferon, interf infectious bursal disease virus VP3 infectious bursal disease virus VP3 eron gamma, Stem cell factor (or known as mast cell growth factor, or c-kit ligand protein), leukemia inhibitory factor, oncostatin M, pleiotrophin, secretory leukocyte protease inhibitor, stem cell factor, tumor necrosis factors, soluble TNF receptors and immunostimulating sequence (ISS).

The isolated nucleic acid may be under the control of an endogenous upstream promoter, or it may be put under control of a heterologous upstream promoter. Promoters include but are not limited to the following: cytomegalovirus, Rous Sarcoma Virus, synthetic pox viral promoter, pox synthetic late promoter 1, pox synthetic late promoter 2 early promoter 2, pox 01L promoter, pox 14L promoter, pox 13L promoter; pox 12L promoter, pox IlL promoter, pox DlOR promoter, PRV gX, HSV-1 alpha 4, chicken beta-actin promoter, HCMV immediate early, MDV gA, MDV gB, MDV gD, ILT gB, BHV-1.1 VP8 and ILT gD and internal ribosomal entry site promoter. In a preferred embodiment the promoter is a human cytomegalovirus promoter.

As provided herein, the vaccine may be used for administration to an avian having an avian pathogen or disease. Such pathogens or diseases are known to those skilled in the art and include but are not limited to: Infectious Bursal Disease Virus, Newcastle Disease Virus, Mycoplasma gallisepticum, Mycoplasma synoviac, Salmonella enteritidis, Salmonella typhimurium, *E. coli,* Riemerella anatipestifer, Tuberculosis (*Mycobacterium avium*), Infectious Coryza, Campylobacter, *Staphylococcus aureus, clostridium,* Erysipelothrix, Chlamydia, Marek's disease virus, Retroviridae (avian leukosis virus), Infectious Bronchitis Virus, Laringotrachitis Virus, Avian Encephalomyelitis Virus, Influenza Virus, Hemorrhagic Enteritis Virus, Egg Drop Syndrome Virus, Pox Virus, Duck Hepatitis Virus, Duck Virus Enteritis, Reoviruses, Goose Parvovirus, Israel Turkey meningoencephalitis Virus (Flaviviridae). In a preferred embodiment the disease is infectious Bursal Disease Virus.

Suitable carriers for the vaccine are well known to those skilled in the art and include but are not limited to proteins, sugars, etc. One example of such a suitable carrier is a physiologically balanced culture medium containing one or more stabilizing agents such as hydrolyzed proteins, lactose, etc. Preferably, the live vaccine is created by taking tissue culture fluids and adding stabilizing agents such as stabilizing hydrolyzed proteins. Further, as used herein "acceptable carrier" are well known to those skilled in the art and include, but are not limited to, 0.01–0.1M and preferably 0.05M phosphate buffer or 0.8% saline.

Additionally, such pharmaceutically acceptable carrier may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example antimicrobials, antioxidants, chelating agents, inert gases and the like.

Further, the vector DNA may be affixed to gold particles delivered into a defeathered area of breast with the use of a helium pulse gene gun. In addition, an effective method to enhance DNA plasmid incorporation into antigen presenting cells is to deliver intramuscularly Cardiotoxin purified from venum of Naja nigricollis prior to plasmid DNA injection.

The term "adjuvant" refers to a compound or mixture that enhances the immune response to an antigen. An adjuvant can serve as a tissue depot that slowly releases the antigen and also as a lymphoid system activator that non-specifically enhances the immune response (Hood et al., *Immunology, Second Ed.,* 1984, Benjamin/Cummings: Menlo Park, Calif., p. 384). Often, a primary challenge with an antigen alone, in the absence of an adjuvant, will fail to elicit a humoral or cellular immune response. Adjuvants include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, dinitrophenol, and potentially useful human adjuvants such as BCG (bacille Calmette-Guerin) and *Corynebacterium parvum).*

The present invention provides a method for enhancing an avian immune response which comprises administering to the avian an effective amount of the vaccine for protecting an avian against an infectious bursal disease virus which comprises an effective immunizing amount of a vector comprising 1) one or more isolated nucleic acids encoding an infectious bursal disease virus polypeptide, wherein said nucleic acid is under the control of a promoter; and 2) a suitable carrier and/or an adjuvant.

In one embodiment the isolated nucleic acid encodes infectious bursal disease virus VP1. In one embodiment the isolated nucleic acid encodes infectious bursal disease virus VP1s1. In one embodiment the isolated nucleic acid encodes infectious bursal disease virus VP1s2. In one embodiment the isolated nucleic acid encodes infectious bursal disease virus VP2. In another embodiment the isolated nucleic acid encodes infectious bursal disease virus VP2S. In another embodiment the isolated nucleic acid encodes infectious bursal disease virus VP3. In another embodiment the isolated nucleic acid encodes infectious bursal disease virus VP4. In another embodiment the isolated nucleic acid encodes infectious bursal disease virus VP5. In another embodiment the vaccine comprises two or more of the infectious bursal disease virus VP1–5. Further the vaccine may comprise one or more of the vectors which have been linearized by appropriate digestion at particular restriction nuclease sites.

The isolated nucleic acid encoding infectious bursal disease virus VP2 is set forth in SEQ ID NO.1 as shown in FIG. 2. The isolated nucleic acid encoding infectious bursal disease virus VP2S is set forth in SEQ ID NO.2 as shown in FIG. 3. The isolated nucleic acid encoding infectious bursal disease virus VP5 is set forth in SEQ ID NO.3 as shown in FIG. 4. The isolated nucleic acid encoding infectious bursal disease virus VP4s is set forth in SEQ ID NO.4 as shown in FIG. 5.

The present invention also provides a method of immunizing an avian comprising administrating to the avian an effective amount of the vaccine. The vaccine may be used for administration to an avian having an avian pathogen or disease. Such pathogens or diseases are known to those skilled in the art and include but are not limited to: Infectious Bursal Disease Virus, Newcastle Disease Virus, and/or Mycoplasma gallisepticum. The vaccine may be administered in conjunction with live or attenuated vaccines which are known to those skilled in the art. As contemplated herein the present vaccine or vector may be administered in combination with other vaccines which are known to those skilled in the art.

For purposes of this invention, an "effective immunizing amount" of the vaccine of the present invention is within the range of 1 ug to 100 mg. In another embodiment the immunizing amount is of 1 ng to 100 ng. In a preferred embodiment the immunizing amount is 100 ug.

The method comprises administering to the animal an effective immunizing dose of the vaccine of the present invention. The vaccine may be administered by any of the methods well known to those skilled in the art, for example, by intramuscular, subcutaneous, intraperitoneal, intravenous, intranasally, orally, intradermal, intrabursal (just above the chickens vent), inovo, or ocularly. Methods of administration are known to those skilled in the art. For example, U.S. Pat. Nos. 5,693,622; 5,589,466; 5,580,859; and 5,566,064 are hereby incorporated by reference in their entirety.

The present invention also provides a method of immunizing an animal, wherein the animal is a chicken, turkey, goose, duck, pheasant, quail, pigeon and ostrich.

This invention is further illustrated in the Experimental Details section which follows. This section is set forth to aid in an understanding of the invention but is not intended to, and should not be construed to, limit in any way the invention as set forth in the claims which follow thereafter.

EXPERIMENTS DETAILS SECTION

Isolation and purification of IBD viral RNA: Total RNA was isolated from the bursae of Fabricius of chicken in IBDV outbreak by the method of Charnczynski and Sechi method Anal. Biochem., 162:156–159 (1987) with modification. Tissue (50 100 mg) was homogenize in 0.5 ml of guanidinium isothiocyanate. The mixture was extracted with 0.5 ml of phenol chloroform (1:1). RNA present in the aqueous phase was precipitated by mixing with 0.5 ml isopropanol at room temperature for 10 min and then centrifuged at high speed for 15 minutes at 4c. The RNA pellet was washed with 75% ethanol and dissolved in 20 pl of nuclease free water. The IBDV cDNA was isolated from bursas of sick chickens in a disease outbreak in Israel. Bursas were obtained and are available from the Kimron Veterinary Institute, Belt-Dagan, Israel, the chicken and fish department.

Specific primers design: Selected primers with high homology to published IBDV gene sequences (Gene Bank) were synthesized. The primers were designed to prime cDNA synthesis of the VP5 complete gene sequence, VP2 complete gene sequence, part of the VP2 gene sequence (VP2S). All the primers include restriction enzyme sites to improve cloning efficiency. The 5' end primers (+) include natural ATG site of the gene open reading frame and the 3' end primers (−) include two stop codons. In the case of VP5 the first stop codon is natural. For VP4 and VP4S-part of VP4 sequence, the 5' end primers (+) include the last ATG site of VP2 gene and the 3' end primers (−) include two stop codons. In the case of VP5 the 5' end primer (+) include the last ATG site of VP4 gene and the 3' end primer (−) includes two stop codons, the first being natural.

Synthesis of First strand specific cDNAs and its amplification: RT-PCR and amplification of cDNA were performed in the same tube using the specific primers. Selected primers building specifically the 5 and 3 of each fragment were chosen for each reaction. The reaction mixture was 50 ul and contained 0.2 Mm dNTP, 1 uM of each primer (downstream and upstream), 1 mM MgSO4, 5u AMV Reverse Transcriptase 5u Tfl DNA. Polymerase, 4–8 ug total RNA, in 1x buffer (Promega Biotec from kit Access RT-PCR system).

The synthesis of the first strand was carried out for 47 min in 48C followed with 2 min at 94c for the enzyme inactivation and RNA/cDNA/primer denaturation. Second strand cDNA synthesis and PCR amplification was preformed for 45 cycles I 30 seconds at 94c denaturation, 56c for 3 min annealing extension at 68c was performed for 2 min for VP2S, VP4S and VP5 and 5 min for VP2, VP4 and VP3 extension. Final extension was carried for 7 min at 68c. The PCR amplification products corresponding to the different reactions were separated on 0.8% agarose gel. (Maniatis. T. et.al., Molecular Cloning: A Laboratory, Manual, Cold Spring Harbor Laboratory, N.Y. (1982). 500 b.p. ladder (Bio Rad) or DNA mass & size standards (FINNZYMES) were used as molecular size markers.

The following primers were used: Primer 1: at the area of the Polyprotein ATG open reading frame site (+) R.F EcorI 5' CCG.GAATTC, CAA ACG ATC GCA GCG ATG ACA AAC3'; Primer 2: at the conserved area of VP2 (−) R.E: NotI 5' ATAAGAAT.GCGGCCGC.TCA TTA ATC TGT CAG TTC ACT CAG GCT TCC 3'; Primer 3: at the end of VP2 (−) R.E: NotI 5' ATAAGAAT.GCGGCCGC TCA TTA CCT CCT TAT GGC CCG GAT TAT GTC 3'; Primer 4: at the end of VP4 (−) R.E: NotI 5'ATAAGAAT.GCGGCCGC TCA TTA GCG TGG ATT GTG AGG GAA ACG TTT3; Primer 5: at the area of the open reading frame of VP5 (+) R.E: BamHI 5'CGC.GGATCC.G CTA TCA TTG ATG GTT AGT AGA GAT CA 3; Primer 6: at the VP5 stop codon area (−)

R.E: EcorI 5'CCG. GAATTC. TTA TCA CTC AGG CTT CCT TGG AAG GTC 3'; Primer 7: at VP2 last M (1301) (+) R.E: EcorI 5'CCGGAATTC. CAC TGA CTT TCG CGA GTA CTT CAT G 3': Primer 8: at VP4 (1840) (−) R.E: NotI 5'ATAAGAATGCGGCCGC. TCA TTA GAG AGT TCG TAT GAA GGA TCC TCT T 3'; Primer 9: at VP4 last M (2052) (+) R.E: EcorI 5'CCGGAATTC, GCC ATG ACG GGA GCC CTC AAG G 3'; Primer 10: at the end of VP3 (3078) (−) R.E: NotI 5'ATAAGAATGCGGCCGC TTA TCA CTC AAG GTC CTC ATC AGA GAC A 3'

Reaction with primers 1 and 2 . . . Reaction with primers 5 and 6, corresponding to 5' and 3' ends VP5, resulted in an amplified DNA segment compatible with its predicted size (150 bp). Reaction with primers 7 and 8 corresponding to 5' and 3' ends VP4S resulted in an amplified DNA segment compatible with its predicted size 540 b.p. Reaction with primers 7 and 4 corresponding to 5' and 3' ends VP4 resulted in an amplified DNA segment compatible with its predicted size 850 b.p. Reaction with primers 9 and 10 corresponding to 5' and 3' ends VP3 resulted in amplified DNA segment compatible with its predicted size 1026 b.p. The PCR products were cleaned with PCR purification kit from Qiagen.

Ligation of DNA fragments to a vector: The amplified cDNA fragments corresponding to VP2S, VP2 VP5 VP4, VP4S and VP3 were cleaved at the restriction sites introduced by the primers during synthesis (EcorI and NotI for VP2, VP2S, VP4 VP4S and VP3 Bam HI and EcorI for VP5). The digested fragments were recovered from the gel by using GenElute column (Supelco) and ligated to the pcDNA3-1 plasmid (Invitrogene) that had also been digested with the corresponding restriction enzymes. Ligation was carried out in the presence of T4 ligase (Miniatis T. et. al., Molecular Cloning: A Laboratory Manual, Cold Spring H&bar Laboratory, N.Y. (1982).

Transformation of bacterial host with the recombinant vector and screen of recombinant Clones: Competent cells *E. coli* DH5α sub-clanning efficiency (Gibco BRL) were used for transformation according to the supplier recommendation Ampicillin resistant clonies were grown in 5 ml Luria-Bertani (LB) broth overnight. Plasmid DNA was isolated using prep PERFECTprep plasmid DNA Kit (5'prime3'prime, INC) Analysis for the viral specific sequences was carried out by digestion of the recombinant plasmid with restriction enzymes, VP2, VP2S, VP4, VP4S and VP3 by EcorI and NotI, VP5 by BamHI and EcorI. 500 b.p. ladder (Bio Rad) or DNA mass & size standards (FINNZYMES) were used as size markers.

Sequencing of VP5, VP2S, VP2 VP4, VP4S and VP3 fragments and comparison with other published sequences: The nucleotide sequence of the cDNA clones was determined by a modification of the didioxy chain termination method (Sanger F. et al, Proc. Natl. Acad. Sci 74 5463–5467 (1977)) using ABI 373 DNA sequencer and ABI Prism DNA sequencing kit from the Perkin-Elmer Corporation. The sequencing was performed with T7 promoter and BGH reverse primer from invitrogen and oligo located on b.p No. 381 on VP2 sequence (see primer p381). Primer p381 5'GCTACAACTGCAGGC 3'.

In-Vitro translation of the cloned fragments. The ability of protein synthesis from the cloned fragments was checked by in-vitro translation. In-vitro coupled transcription/translation system TNT Coupled Reticulocyte lysate systems from Promega was used. The detection was preformed by using Transcend Non radioactive Colorimetric translation detection system (Promega) according to the manufacture. Briefly the reaction was carried out using 25 1 TNT Rabbit Reticulocyte lysate, 2 1 of reaction buffer, 1 1 T7 polymerase, 1 1 amino acid mixture 1 mM, 40u RNasin ribonuclease inhibitor, 1 g DNA plasmid template and 3 1 of Transcend Biotin-Lysyl-tRNA at 30c for 90 min. From each translation reaction 1 aliquot was removed and 15 1 of SDS sample buffer (Laemmli, U.K. (1970) Nature (London) 227, 680) was added. The samples were boiled for 2 min and the products were resolved on an SDS-PAGE gel (Laemmli, U.K. (1970) Nature (London) 227, 680). Bio-Rad SDS-PAGE pertained standards (Broad Range Marker) or NOVEX (See Blue pre stained standards) were used as molecular weight markers. The translation products were blotted from the SDS-PAGE to nitrocellulose 0.22 membrane (Towbin, H., Staehelin, T. and Gordon, J. (1979). Proc. Natl. Acad. Sci. USA 76, 4350. The colorimetric (BCIP/NBT) Detection of the protein products was carried out according to Promega. Using VP2 cloned in pcDNA3-1, a protein band of approximately 48 kDa was observed on the blot after developing the colorimetric reaction. The control (empty plasmid) gave none (FIG. 7). Using VP3 and VP4 cloned in pcDNA3.1, protein bands of approximately 40 kDa, and 33 kDa, respectively were observed on the blot. The control gave none (FIG. 7*a*).

Immunization of chickens against IBDV: To test the ability of the DNA plasmids to protect against IBDV challenge, groups of one day old chicks (15–16 animals in each) were immunized with plasmids containing sequences coding for VP2S, VP2, VP5 (SEQ ID NO.2, SEQ ID NO.1 SEQ ID NO.3 respectively), a mixture of VP2S, VP2, VP5, an empty plasmid and PBS. Each chick received 100 μg of plasmid DNA intramuscularly in 200 μl PBS. Another group was injected with inactivated IBDV commercial vaccine. On day 14 the chicks were bled and boosted with 100 μg DNA in 300 μl PBS intramuscularly. At the age of 35 days the birds were bled and challenged intraorbitally with 1:10 dilution of an extract (1:1 w/v), prepared from bursas of chicks infected with IBDV isolate characterized above.

At the age of 39 days (4 days after challenge) half of the chicks were weighted and sacrificed. The other half was bled weighted and sacrificed on day 43 (8 days after challenge). Body weights of birds sacrificed on both days are presented in Table 1. Antibody titers against IBDV were measured before and after challenge using FlockChek ELISA test kit (IDEXX). Titer a and b represent two independent ELISA at 1:500 dilution and titer a–b represent the mean of the two experiments. Results are presented in Table 1.

No statistically significant difference in antibody titer was found between treated and control groups before challenge (day 35) (unshown results). Groups representing plasmids containing coding sequences for VP2S and VP2 responded to IBDV challenge with specific antibody titer significantly higher than groups receiving empty plasmid or PBS. The results were analyzed statistically using ANOVA test. Significance of F ratio in ANOVA is presented, testing the hypothesis that all groups are similar (this hypothesis is rejected when $P(F)<0.05$). Group means within measurements with no common superscript differ significantly according to a t test conducted separately for each pair of groups (Table 1).

Whereas 4 days after virus challenge there was no significant difference between the body weight of the chicks in the different groups (ANOVA P(F)’0.303), 8 days after challenge chicks vaccinated with VP2 and VP2S had shown higher body weight compared to chicks vaccinated with empty plasmid or PBS (ANOVA P(F)’0.018).

The above results prove that chickens immunized with DNA vaccines to VP2 and VP2S (plasmids containing DNA sequences encoding for these peptides) can elicit antibody response to the peptides encoded by the plasmids and also confer protection against the virus as reflected by the significant higher weight gain of immunized compared with unimmunized chicks.

TABLE 1

| Group | Four days after infection | | Eight days after infection | | | | | | Titer |
|---|---|---|---|---|---|---|---|---|---|
| | n[1] | BW, g | n[1] | BW, g | n[1] | Titer a | n[1] | Titer b | n[1] | a + b |
| VP$_2$S | 7 | 293 | 6 | 394$^{ab}$ | — | — | 5 | 3133$^{bc(a)3}$ | — | — |
| VP$_2$ | 8 | 266 | 7 | 368$^{abc}$ | 6 | 3019$^a$ | 6 | 3363$^{b(a)}$ | 6 | 3191$^a$ |
| VP$_5$ | 7 | 256 | 8 | 361$^{bc}$ | — | — | — | — | — | — |
| MIX | 7 | 273 | 8 | 360$^{bc}$ | 5 | 2404$^{ab}$ | — | — | — | — |
| PLASMID | 8 | 265 | 6 | 332$^c$ | 5 | 1983$^b$ | 5 | 2294$^{cd(b)}$ | 5 | 2139$^b$ |
| INACTIVATED IBDV | 7 | 290 | 7 | 411$^a$ | — | — | 7 | 5042$^a$ | — | — |
| PBS | 6 | 259 | 5 | 335$^c$ | — | — | 5 | 2119$^{d(b)}$ | — | — |
| P(F)$^2$ | — | 0.303 | — | 0.018 | — | 0.017 | — | 0.001 | — | 0.007 |
| Mean | 50 | 272 | 47 | 367 | 17 | 2503 | 28 | 3265 | 11 | 2712 |
| SD | — | 34.3 | — | 41.7 | — | 516 | — | 768 | — | 605 |

$^{abc,\cdots}$ Group means within measurement with no common superscript differ significantly (P<0.05) according to a t test conducted separately for each pair of groups
[1] n' number of chicks in each group for the analyzed measurement
[2] Significance of F ratio in ANOVA, testing the hypothesis that all groups are similar (this hypothesis is rejected when P(F)<0.05)
[3] The superscripts in parenthesis indicates the significance of differences obtained in analysis without Group No. 6

Microscopic pathology: Samples of the Bursa of Fabricius were fixed in 10 percent formalin. Samples were embedded in paraffin wax, sectioned at 6 μm and stained with haematoxylin and cosin. Bursas were sampled at the end of the experiment, 8 days after challenge. 7 Bursas were sampled from experimental group 2 (VP2), 7 from group 6 (conventional inactivated vaccine) and 6 from group 5 (control empty plasmid). Samples were evaluated for the degree of bursal atrophy by light microscopy evaluation.

The following results were noted:

| | Marked lymphoid depletion | moderate lymphoid depletion | Mild lymphoid depletion | No signs of lymphoid depletion |
|---|---|---|---|---|
| Group 5 | 4/6 (67%) | 2/6 (33%) | | |
| Group 6 | | 1/7 (14%) | 4/7 (57%) | 2/7 (29%) |
| Group 2 | | 7/7 (100%) | | |

The degree of lymphoid depletion reflects the intensity of bursal atrophy due to IBDV infection. Group 5, control empty plasmid, was the most severely affected. Most of the samples examined showed marked atrophy. Group 6 was moderately affected. The clear difference between groups 5 and 2 reflects a protective effect of the VP2 plasmid vaccine. Most of the samples from group 6 showed mild to no bursal atrophy.

What is claimed is:

1. A vector comprising an isolated nucleic acid encoding an infectious bursal disease virus VP2 polypeptide as set forth in SEQ ID NO:1, wherein the expression of said VP2 polypeptide is under the control of a promoter.

2. The vector of claim 1, wherein promoter is Rous Sarcoma Virus promoter, pox viral promoter, pox late promoter 1, pox late promoter 2 early promoter 2, chicken beta actin promoter, pox 01L promoter, pox 14L promoter, pox 13L promoter, pox 12L promoter, pox IL promoter, pox E1OR promoter, PRV gX, HSV-1 alpha 4, HCMV immediate early, MDV gA, MDV gB, MDV gD, ILT gB, BHV-1, 1 VP8 or ILT gD.

3. The vector of claim 1, designated P-INN-001, deposited with the American Type Culture Collection under ATCC Accession No.:PTA-1101.

4. A vaccine for protecting an avian species against infectious bursal disease virus, said vaccine comprising 1) a vector comprising an isolated nucleic acid encoding an infectious bursal disease virus VP2 polypeptide as set forth in SEQ ID NO:1, wherein the expression of said VP2 polypeptide is under the control of a promoter; and 2) a suitable carrier.

5. The vaccine of claim 4, wherein said promoter is a heterologous upstream promoter or an endogenous upstream promoter.

6. The vaccine of claim 4, wherein said promoter is Rous Sarcoma Virus promoter, pox viral promoter, pox late promoter 1, pox late promoter 2 early promoter 2, chicken beta actin promoter, pox 01L promoter, pox 14L promoter, pox 13L promoter, pox 12L promoter, pox IL promoter, pox E1OR promoter, PRV gX, HSV-1 alpha 4, HCMV immediate early, MDV gA, MDV gB, MDV gD, ILT gB, BHV-1, 1 VP8 or ILT gD.

7. The vaccine of claim 4, wherein the vector is designated P-INN-001, deposited with the American Type Culture Collection under ATCC Accession No.: PTA-1101.

8. A method of stimulating or increasing an immune response of an avian species against infectious bursal disease virus, said method comprising the step of administration to said avian species the vaccine of claim 4, said vaccine administered n an amount effective to stimulate or increase an immune response against infectious bursal disease virus in said avian species.

9. A method of immunizing an avian species against infectious bursal disease virus, said method comprising the step of administration of said avian species the vaccine of claim 4, said vaccine administered in an amount effective to immunize said avian species against infectious bursal virus.

10. The method of claim 9, wherein the administration is intramuscular, subcutaneous, intraperitoneal, intravenous, intranasal, oral, intradermal, in ova, intrabursal or ocular.

* * * * *

SEQUENCE LISTING

<160> NUMBER OF SEQ ID NOS: 4

<210> SEQ ID NO 1
<211> LENGTH: 1365
<212> TYPE: DNA
<213> ORGANISM: Infectious bursal disease virus

<400> SEQUENCE: 1

```
atgacaaacc tgcaagatca aacccaacag attgttccgt tcatacggag ccttctgatg      60
ccaacaaccg gaccggcgtc cattccggac gacaccctag agaagcacac tctcaggtca     120
gagacctcga cctacaattt gactgtgggg gacacagggt cagggctaat tgtcttttc     180 cctggtttcc ctggctcaat tgtgggtgct cactacacac tgcagagcaa tgggaactac     240
aagttcgatc agatgctcct gactgcccag aacctaccgg ccagctacaa ctactgcagg     300
ctagtgagtc ggagtctcac agtgaggtca agcacactcc ctggtggcgt ttatgcacta     360
aatggcacca taaacgccgt gaccttccaa ggaagcctga gtgaactgac agatgttagc     420
tacaatgggt tgatgtctgc aacagccaac atcaacgaca aaatcgggaa cgtcctagta     480
ggggaagggg taaccgtcct cagcttaccc acatcatatg atcttggta tgtgagactc     540
```

-continued

```
ggtgacccca ttcccgctat agggctcgac ccaaaaatgg tagcaacatg tgacagcagt        600
gacaggccca gagtctacac cataactgca gccgatgatt accaattctc atcacagtac        660
caagcaggtg gggtaacaat cacactgttc tcagctaaca tcgatgccat acaagcctc         720 agcatcgggg gagaactcgt gttccaaaca agcgtccaag gccttatact gggtgctacc        780 atctaccta taggctttga tgggactgcg gtaatcacca gagctgtggc cgcagacaat        840
gggctaacgg ccggcactga caaccttatg ccattcaata ttgtgattcc aaccagcgag        900
ataacccagc caatcacatc catcaaactg agatagtga cctccaaaag tggtggtcag         960
gcgggggatc agatgtcatg gtcagcaagt gggagcctag cagtgacgat ccacggtggc       1020
aactatccag gggccctccg tcccgtcaca ctagtagcct acgaaagagt ggcaacagga       1080
tctgtcgtta cggtcgccgg ggtgagcaac ttcgagctga tcccaaatcc tgaactagca       1140
aagaacctgg tcacagaata cggccgattt gacccaggag ccatgaacta cacaaaattg       1200
atactgagtg agagggaccg tcttggcatc aagaccgtat ggccaacaag ggagtacact       1260
gactttcgcg agtacttcat ggaggtggcc gacctcaact ctcccctgaa gattgcagga       1320
gcatttggct tcaaagacat aatccgggcc ataaggaggt aatga                       1365
```

<210> SEQ ID NO 2
<211> LENGTH: 420
<212> TYPE: DNA
<213> ORGANISM: Infectious bursal disease virus

<400> SEQUENCE: 2

```
atgacaaacc tgcaagatca aacccaacag attgttccgt tcatacggag ccttctgatg         60
ccaacaaccg gaccggcgtc cattccggac gacaccctag agaagcacac tctcaggtca       120
gagacctcga cctacaattt gactgtgggg gacacaggt caggctaat tgtcttttt         180 cctggttcc ctggctcaat tgtgggtgct cactacacac tgcagagcaa tgggaactac       240
aagttcgatc agatgctcct gactgcccag aacctaccgg ccagctacaa ctactgcagg       300
ctagtgagtc ggagtctcac agtgaggtca agcacactcc ctggtggcgt ttatgcacta       360
aatggcacca taaacgccgt gaccttccaa ggaagcctga gtgaactgac agattaatga       420
```

<210> SEQ ID NO 3
<211> LENGTH: 440
<212> TYPE: DNA
<213> ORGANISM: Infectious bursal disease virus

<400> SEQUENCE: 3

```
atggttagta gagatcagac aaacgatcgc agcgatgacg aacctgcaag atcaaaccca        60
acagattgtt ccgttcatac ggagccttct gatgccaaca accgaccggc gtccattccg       120
gacgacaccc tagagaagca cactctcagg tcagagacct cgacctacaa tttgactgtg       180
ggggacacag gtcagggct aattgtctt ttccctggtt tccctggctc aattgtgggt       240
gctcactaca cactgcagag caatgggaac tacaagttcg atcagatgct cctgactgcc       300
cagaacctac cggccagcta caactactgc aggctagtga gtcggagtct cacagtgagg       360
tcaagcacac tccctggtgg cgtttatgca ctaaatggca ccataaacgc cgtgaccttc       420
caaggaagcc tgagtgataa                                                    440
```

<210> SEQ ID NO 4
<211> LENGTH: 537
<212> TYPE: DNA

-continued

```
<213> ORGANISM: Infectious bursal disease virus

<400> SEQUENCE: 4
atggaggtgg ccgacctcaa ctctcccctg aagattgcag gagcatttgg cttcaaagac      60
ataatccggg ccctaaggag gatagctgtg ccggtggtct ctacattgtt cccacccgcc     120
gctcccctag cccatgcaat tggggaaggt gtagactacc tgctgggcga tgaggcacaa     180
gctgcttcag gaactgctcg agccgcgtca ggaaaagcaa gagctgcctc aggccgcata     240
aggcagctaa ctctcgccgc cgacaagggg tacgaggtag tcgcgaatct gtttcaggtg     300
ccccagaatc ctgtagtcga cgggattctc gcctcacctg ggatactccg cggcgcacac     360
aacctcgact gcgtgttgag agagggtgcc acgctattcc ctgtggtcat cacgacagtg     420
gaagatgcca tgacacccaa agcactgaac agcaaaatgt ttgctgtcat tgaaggcgtg     480
cgagaagatc tccaacctcc atctcaaaga ggatccttca tacgaactct ctaatga       537
```